US009104789B2

(12) United States Patent
Gross et al.

(10) Patent No.: US 9,104,789 B2
(45) Date of Patent: Aug. 11, 2015

(54) PATIENT MONITORING WITH AUTOMATIC RESIZING OF DISPLAY SECTORS

(75) Inventors: Brian D. Gross, North Andover, MA (US); Soren S. Johnson, Wakefield, MA (US); W. Scott Reid, Derry, NH (US); Elizabeth Zengo, Hudson, NH (US)

(73) Assignee: KONINKLIJKE PHILIPS ELECTRONICS N.V., Eindhoven (NL)

( * ) Notice: Subject to any disclaimer, the term of this patent is extended or adjusted under 35 U.S.C. 154(b) by 0 days.

(21) Appl. No.: 13/377,833

(22) PCT Filed: May 17, 2010

(86) PCT No.: PCT/IB2010/052184
§ 371 (c)(1),
(2), (4) Date: Dec. 13, 2011

(87) PCT Pub. No.: WO2011/001302
PCT Pub. Date: Jan. 6, 2011

(65) Prior Publication Data
US 2012/0095778 A1 Apr. 19, 2012

Related U.S. Application Data

(60) Provisional application No. 61/221,109, filed on Jun. 29, 2009.

(51) Int. Cl.
*G06Q 50/22* (2012.01)
*G06Q 50/24* (2012.01)
*G06F 19/00* (2011.01)

(52) U.S. Cl.
CPC ............ *G06F 19/3406* (2013.01); *G06Q 50/22* (2013.01)

(58) Field of Classification Search
USPC .................................. 128/920; 345/660–671
IPC .................................. G06F 19/00; G06Q 50/22
See application file for complete search history.

(56) References Cited

U.S. PATENT DOCUMENTS

| 5,262,944 | A | 11/1993 | Weisner et al. |
| 5,319,363 | A | 6/1994 | Welch et al. |
| 7,460,905 | B2 * | 12/2008 | Mase et al. ..................... 600/544 |
| 8,510,126 | B2 * | 8/2013 | Martin et al. ..................... 705/2 |

(Continued)

FOREIGN PATENT DOCUMENTS

| EP | 0569670 A2 | 11/1993 |
| EP | 1852060 A1 | 11/2007 |

(Continued)

OTHER PUBLICATIONS

IBM Technical Disclosure Bulletin;Transluscent Windows for Graphical-User Interfaces; 1994; vol. 37; No. 04B; pp. 101-102.

*Primary Examiner* — John Pauls
*Assistant Examiner* — Jason Tiedeman
(74) *Attorney, Agent, or Firm* — Fay Sharpe LLP

(57) ABSTRACT

A patient monitoring station includes a display that displays a plurality of sectors. A controller displays the patient data received from one or more remote medical devices in a corresponding sector of the display. The controller is programmed to collapse one or more sector in response to one of (1) not receiving patient data from the corresponding remote patient monitor or (2) receiving patient data not indicative of a pending patient event or alarm condition; and expand at least sectors that receive patient data indicative of a pending patient event or alarm condition.

19 Claims, 5 Drawing Sheets

(56) References Cited

U.S. PATENT DOCUMENTS

| | | |
|---|---|---|
| 2005/0188083 A1 | 8/2005 | Biondi et al. |
| 2005/0229110 A1* | 10/2005 | Gegner et al. ............... 715/800 |
| 2008/0221418 A1 | 9/2008 | Al-Ali et al. |
| 2008/0262870 A1* | 10/2008 | Jones et al. ..................... 705/2 |
| 2009/0054735 A1* | 2/2009 | Higgins et al. ............... 600/300 |
| 2009/0054743 A1 | 2/2009 | Stewart |
| 2009/0313076 A1* | 12/2009 | Schoenberg ..................... 705/9 |
| 2010/0079490 A1 | 4/2010 | Terazono et al. |

FOREIGN PATENT DOCUMENTS

| | | |
|---|---|---|
| JP | 2007018187 A | 1/2007 |
| JP | 2008188214 A | 8/2008 |
| JP | 2009055476 A | 3/2009 |
| WO | 03091836 A2 | 11/2003 |

\* cited by examiner

PATIENT MONITORING WITH AUTOMATIC RESIZING OF DISPLAY SECTORS

CROSS REFERENCE TO RELATED APPLICATIONS

This application claims the benefit of U.S. provisional application Ser. No. 61/221,109 filed Jun. 29, 2009, which is incorporated herein by reference.

The present application relates to medical monitoring and clinical data display devices for monitoring the physiological condition of a patient. It finds particular application in improving the configuration and accessibility of patient information on a patient monitoring, central station monitor or multi-patient dashboard display device and will be described with particular reference thereto.

Presently, central station or other multi-patient monitoring devices have a fixed area or sector of a display assigned to each patient bed. The monitoring sectors display the patient's identification, monitored physiological data, status, alarms, and the like. If no patient is in the bed, the sector is blank but remains allocated. Each sector typically displays several physiological parameters for each patient, such as an EGG signal, a respiration signal, pulse rate, blood pressure, SpO2, and other indicators of patient health or well being, and the like. As more physiological parameters are monitored, the displayed information is compressed or displayed in a smaller harder to read size, or the like in order to fit in the fixed sector assigned to the patients. As simple patient worn physiological parameter measuring devices become more widely available, more and more physiological parameters are being measured for each patient.

The present application provides a new and improved patient monitoring device which overcomes the above-referenced problems and others.

In accordance with one aspect, a patient monitoring station is provided. A display displays a plurality of sectors. A controller displays the patient data received from one or more remote medical devices in a corresponding sector of the display. The controller is programmed to or including means to expand at least sectors that receive patient data indicative of a pending patient event or alarm condition and at least one of display the expanded sector at least partially transparent, or collapse one or more sectors in response to one of (1) not receiving patient data from the corresponding remote patient monitor or (2) receiving patient data not indicative of a pending patient event, caregiver workflow, change in health state, or alarm condition.

In accordance with another aspect, a method of displaying medical parameters is provided. Medical parameters received from one or more remote medical devices are displayed in a corresponding sector of a display. Sectors of the display are collapsed in response to one of (a) the corresponding remote medical device not sending patient data and (b) the received patient data are not indicating a pending patient event. Sectors of the display are expanded at least in response to the medical parameters received being indicative of a pending patient event.

One advantage resides in the automatic creation of display sectors as needed.

Another advantage resides in the easier readability of physiological data of patients most in need of monitoring.

Another advantage resides in reducing screen clutter and distractions from the physiological data of patients not in current need of attention.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
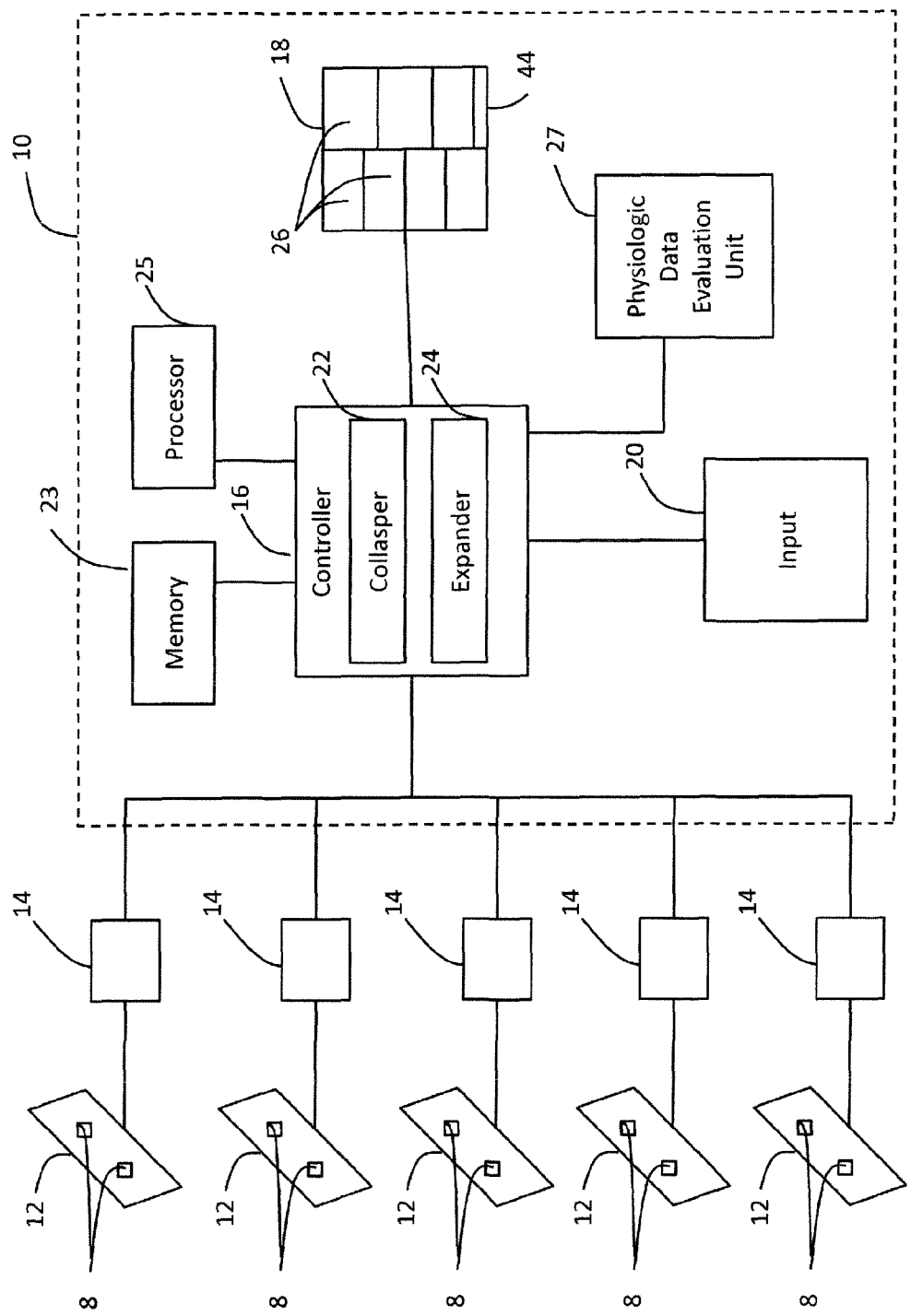
FIG. 1 is a diagrammatic illustration of a patient display monitor in accordance with the present application.

With reference to FIG. 1, a patient monitoring station 10 monitors a plurality of patient beds 12, e.g., in a centralized, multi-patient clinical display station. The patient monitoring station 10 is frequently centrally located in reference to the beds 12 that it monitors, such as a nurse's station, or the like. The patient in each of the patient beds 12 has one or more remote medical devices 8 that measure physiological parameters of the patient and generate physiological data indicative thereof. These remote medical devices 8 include ECG sensors, IV fluid pumps, blood pressure sensors, SpO2 sensors, pulse sensors, thermometers, respiratory sensors, and exhaled gas sensors. Of course, other remote medical devices 8 can be associated with a patient, and not all of the above-mentioned remote medical devices 8 have to be associated with a patient at any given time. As used herein, medical devices signifies data sources indicating patient health or caregiver workflow, e.g., a medical administration scheduler.

The remote medical devices 8 report the measured physiological data to a local buffer 14. The buffer 14 serves as a gathering point for the physiological data measured by the remote medical devices 8, and provides temporary storage for the data. The local buffer 14, for example may be a patient's bedside monitor, a monitor that travels with the patient, such as the transmitter of an ambulatory patient worn monitoring system, or the like. The local buffer 14 may also be a more permanent fixture, such as a wall-mounted monitor that is permanently associated with each bed, a group of beds, or a room. The communication links between the remote medical devices 8 and the local buffer 14 may be wireless, hard wired, or a combination of both. Similarly, the remote medical devices 8 may be powered by battery, external AC power, or a combination of both.

The local buffers 14 communicate with the patient monitoring station 10. The physiological data can be communicated continuously or periodically. For a given patient, some data may be communicated continuously, such as EGG, and other data, such as blood pressure, periodically. A controller 16 receives the measured physiological data from the buffers 14 of as many patient beds 12 for which the patient monitoring station 10 is responsible. The controller 16 then controls a display 18 of the patient monitoring station 10 to display the measured physiological data received from each patient in a corresponding sector 26. The controller 16 automatically creates sectors 26 of the display 18 corresponding to a configured patient bed 12. The patient monitoring station 10 also includes a user interface 20 that allows the user, such as a caregiver, a patient group like a surgical, medical, or covering physician, to view and/or manipulate the data displayed on the display 18. The interface 20 can be a separate component or integrated into the display 18 such as with a touch screen monitor. Additionally, the controller 16 includes a collapsing unit 22 and an expanding unit 24 to control or manipulate the sectors 26 of a display 18 assigned to a particular caregiver, patient, room, device, and so forth. The collapsing 22 and expanding 24 units may include a processor or computer, software, hardware, or the like.

The controller also includes a processor 25, for example, a microprocessor which is configured to execute patient monitoring software for performing the operations described in further detail below and, optionally, collapsing or expanding software. Typically, patient monitoring software will be stored in a memory or a computer readable medium 23 and be executed by the processor 25. Types of computer readable medium 23 include memory such as a hard disk drive, CD-ROM, DVD-ROM and the like. Other implementations of the processor 25 are also contemplated. Display controllers, Application Specific Integrated Circuits (ASICs), and microcontrollers are illustrative examples of other types of component which may be implemented to provide functions of the processor 25. Embodiments may be implemented using software for execution by a processor, hardware, or some combination thereof.

Optionally, a physiological data evaluation unit 27 evaluates the physiological data from each patient and decides whether the patient's sector 26 should be expanded or collapsed. For example, the evaluation checks for alarms, whether each measured parameter is approaching threshold values, whether a trend of any parameter is approaching a threshold, whether any parameter lacks stability or fluxuates too much, combinations of parameters are approaching a threshold, and other indicators that a patient needs more or less medical monitoring. The thresholds include values exceeding a limit based on time, severity, escalation, or the like. The physiological evaluation unit may include a suitable programmed computer or processor, software applied by the processor 25, or the like.

The communications links between the buffers 14 and the patient monitoring station 10 may be wireless. If the buffer 14 is embodied, for example, in a local monitor mounted on an IV stand or worn, the patient can leave the immediate vicinity, taking the buffer 14 along. Wireless communication between the buffer 14 and the patient monitoring station 10 allows greater mobility for the patient while still being able to monitor the selected parameters of the patient. If the buffer 14 is embodied in a more permanent fixture, the communications links between the buffers 14 and the patient monitoring station 10 may be hard lines, such as standard Ethernet network cables.

Figure 2:
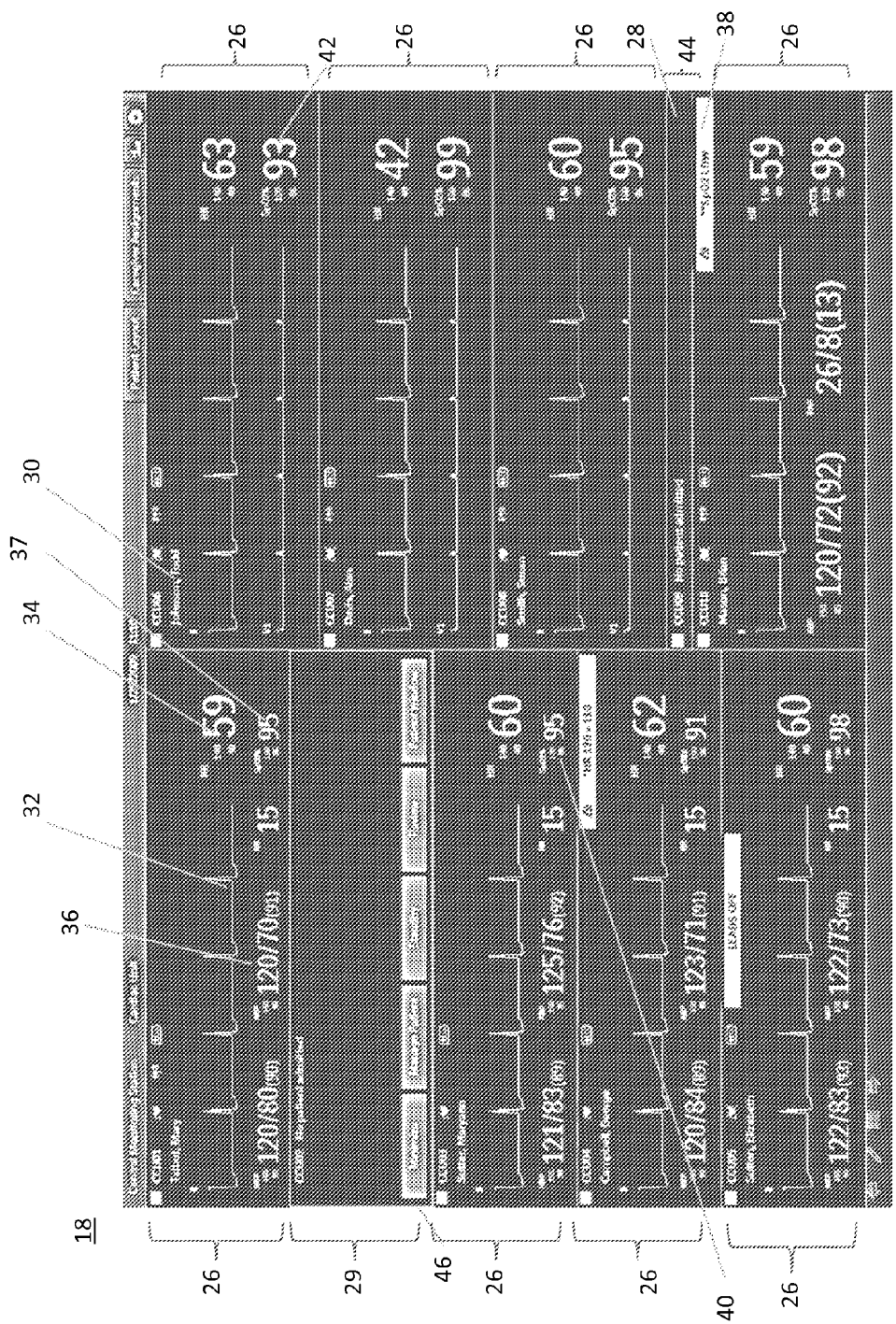
FIG. 2 is a ten sector display with an automatically collapsed sector and a manually collapsed sector.

As mentioned previously, the controller 16 directs the display 18 to display the information received from the various buffers 14. With reference now to FIG. 2, the display 18 of the patient monitoring station 10 is divided into sectors 26, each sector 26 representing information received from one buffer device 14, that is, from one patient. Ten sectors 26 are illustrated in FIG. 2, but more or fewer sectors are also contemplated. The number of sectors 26 per patient monitoring station 10 could be dictated by the size of the display 18, the patient to monitoring station 10 ratios, the number of patient beds 12, and other factors. As illustrated, each of the sectors 26 of the display 18 corresponds to one patient bed. Physiological data associated with each patient is displayed within a corresponding sector 26. When no patient is admitted to a specific bed 12 or the patient monitoring station 10 is not receiving information from a buffer 14, a message 28 is displayed indicating that no patient is admitted. Rather than leaving the empty sector 29 full size, the collapsing unit 22 collapses the empty sector 44 and the expanding unit 24 expands the other sectors 26 to use the space freed up when the sector 44 is collapsed.

The sectors 26 of the display 18 have various sub-displays corresponding to the information received from the buffer 14. For example, the sector 26 has a patient ID sub-display 30 where the patient's name, bed or room number, assigned patient group, caregiver or team, and other identifying information, such as a unique hospital ID are displayed. An ECG sub-display 32 displays the latest ECG readings received from the buffer 14 about the patient. A pulse sub-display 34 displays the latest pulse rate readings of the patient. A blood pressure sub-display 36 displays the latest blood pressure reading from the patient. There may also be SpO2 display 37, end tidal CO2 (etCO2 display), respiration displays, and the like. Typically, due to space limitations, only three or four values can be displayed on the sector 26. Each additional sector 26 displays similar information, with the exception that each sector 26 represents a separate patient. Also, each sector 26 can be configured independently. The processor 25 can be programmed to display different information based on what clinical or workflow condition is present at the time of the event.

The patient monitoring station 10 includes an alarm, such as a visual alarm 38 e.g. in each sector, an audio alarm speaker, or so forth. If one or more of the physiological data exceeds a threshold (such as a trended heart rate going below a lower threshold, or a trended blood pressure going above an upper threshold), then the alarm 38 suitably activates to warn medical personnel of a potential problem with specific alarm information being displayed on display 18. The patient monitoring station 10 also includes an indicator of a pending patient event, such as a visual alarm 40. If one or more of the physiological data exceed a certain predetermined threshold that indicate a possible patient event, such as low battery, leads have come off, or the like, the alarm 40 activates to warn medical personal of a potential event.

The controller 16 of the patient monitoring station 10 controls the display 18 to display the sectors 26 of the display in an expanded format 42 or a collapsed format 44. As illustrated, the upper right sector 26 of the display 18 is displaying the corresponding information received from the buffer 14 in the expanded format 42. The sector 26 with the expanded format 42 displays a full data representation of the information received from the buffer 14 including the patient ID and multiple sub-displays of physiological data and patient statuses as a full or expanded size object on the display 18. The collapsed format sector 44 is configured to display limited data representation of information received from the corresponding buffer 14 as a small object on the display 18. Such limitations can preferably be provided according to personal criteria, e.g. the patient monitors of a care group (which is usually taken care by one nurse or a specific group of nurses), a patient's highest priority physiologic data, or according to locality criteria, e.g. the patient monitors of a specific room in a hospital. This status information is preferably displayed by means of symbols, pictograms, codings, and/or alphanumeric signs. The content of the expanded area could be text only or a combination of symbols, pictograms, codings, and/or alphanumeric signs.

The size and location of the collapsed format 44 and expanded format 42 sectors depends on the specific screen configurations of the display 18. In one embodiment, the size of the collapsed format 44 and expanded format 42 sectors are sized such that all of the collapsed format sectors 44 are of uniform size and all of the expanded format sectors 42 are of uniform size. In yet another embodiment, the collapsed format 44 and expanded format 42 sectors are scaled so that they fit within a boundary of the display 18. In another embodiment, the size of the expanded format 42 sectors is based on the severity of the patient event or alarm condition. Additionally, the size of the expanded format sector 42 can be based on the time that has elapsed since the patient event or alarm condition was encountered. For example, after an alarm condition has been resolved, the sector can shrink gradually over time. The size of the collapsed format 44 and expanded format 42 sectors can also be increased or decreased in size in order to display more detailed information about one or more patients. In one embodiment, the collapsed format 44 and expanded format 42 sectors corresponding to actively monitored patients can only be reduced or increased to a size to a predefined minimum or maximum size in order to still enable the monitoring of the all of the sectors 26 of the display 18. It is also preferred that the expanded format 42 and the collapsed format 44 sectors not overlap each other or only overlap temporarily. The size and automatic window generation can be based on alarm severity as well as time the condition is persistent. Border decoration, background intensity, background transparency, and color can also be used to attract attention to a selected sector(s).

To enable user interfacing and the exchange of monitored physiological data, in addition to the display 18, the patient monitoring station 10 can also include a sector user interface or an input/output (I/O) portion 46 for each sector 26. The sector user interface 46 allows the user to view and/or manipulate the data of each sector 26 displayed on the display 18, e.g. a touch screen display. Alternatively, the monitoring station 10 optionally incorporates a keypad, keyboard, touch sensitive screen, or other user input device (not shown) to enable user input.

In one embodiment, the user interface 46 also allows the user to define specific sectors 26 of the display 18 in an auto-collapse mode, auto-expand mode, or collapse to background mode. In auto-collapse mode, sectors 26 are automatically displayed in a collapsed format 44 upon receiving no physiological data from the corresponding buffer 14, being placed in a standby mode by the controller 16, or through the user selection to configure the sector 26 to an auto-collapse mode. In auto-expand mode, sectors 26 of the display 18 are automatically displayed in an expanded format 42 upon receiving valid physiological data from the buffer 14, receiving physiological data indicative of a pending patient event, or alarm conditions. In a collapse to background mode, the sectors 26 are in a collapsed format 44 and attached to the background of the display 18.

Figure 3:
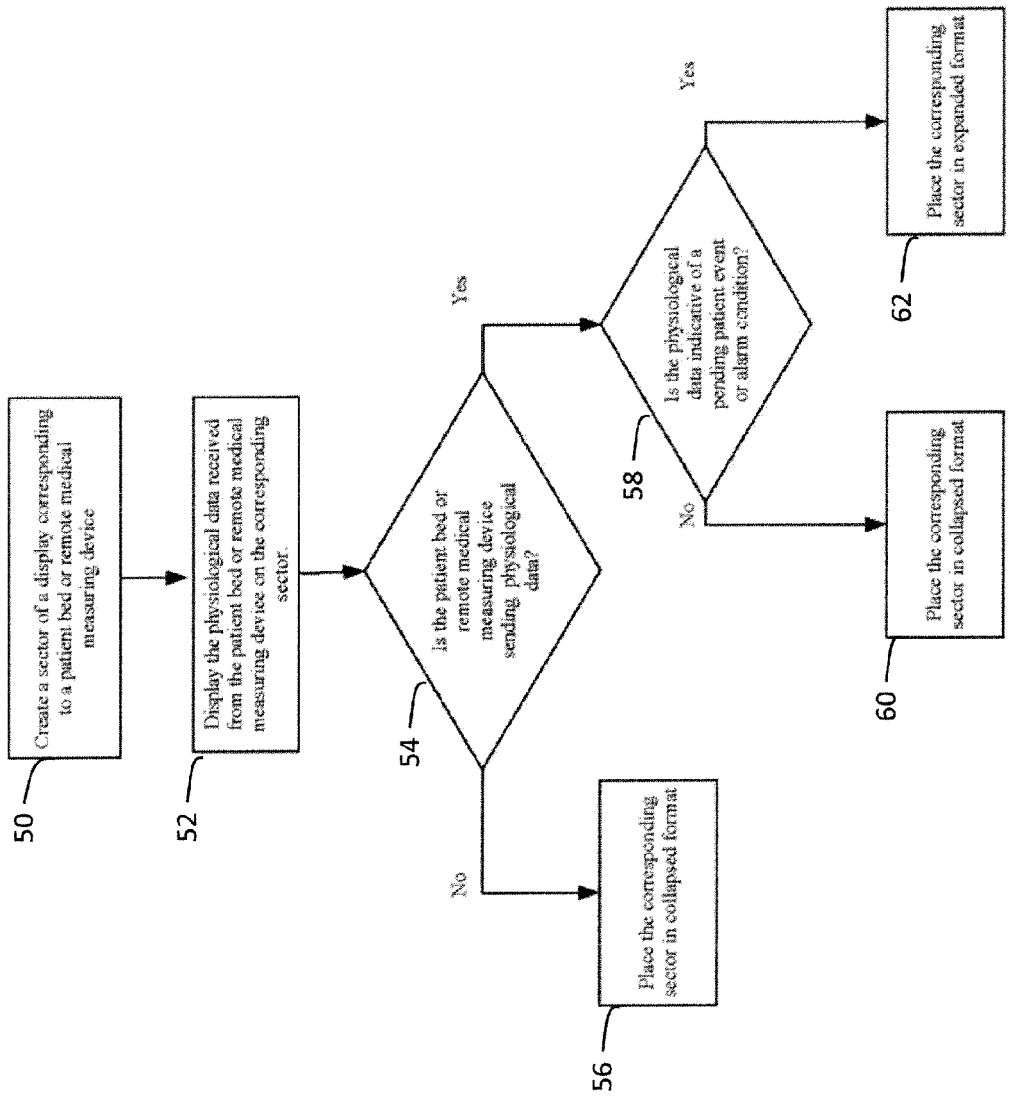
FIG. 3 is a flowchart diagram of the operation of a patient display monitor in accordance with the present application.

FIG. 3 illustrates the core operation of the controller 16 of the patient monitoring system 10. In a step 50, the patient monitoring system 10 automatically creates a sector 26 of a display 18 corresponding to a patient bed 12 or the remote medical device 8. The physiological data received from the patient bed 12 or remote medical device 8 is displayed in the corresponding sector 26 of the display 18 in a step 52. In a step 54, the patient monitoring system 10 determines whether the patient bed 12 or remote medical device 8 is sending or the controller 16 is receiving physiological data from the buffer 14 of the patient bed 12 or remote medical device 8. In response to the patient bed 12 or remote medical device 8 not sending physiological data, the corresponding sector 26 of the display 18 is placed in a collapsed format 44 in a step 56. If the patient bed 12 or remote medical device 8 is sending physiological data, the patient monitoring system 10 determines whether the received physiological data are indicative of a pending medical event or alarm condition in a step 58. In a step 60, the corresponding sector 26 displaying the received physiological data is placed in a collapsed format 44 in response to the physiological data not indicating a pending medical event or alarm condition. In response to the received physiological data indicating a pending medical event or alarm condition, the corresponding sector 26 of the display 18 is placed in an expanded format 42 in a step 62. The controller 16 is or includes a processor which is programmed to perform the steps 50-60.

Figure 4:
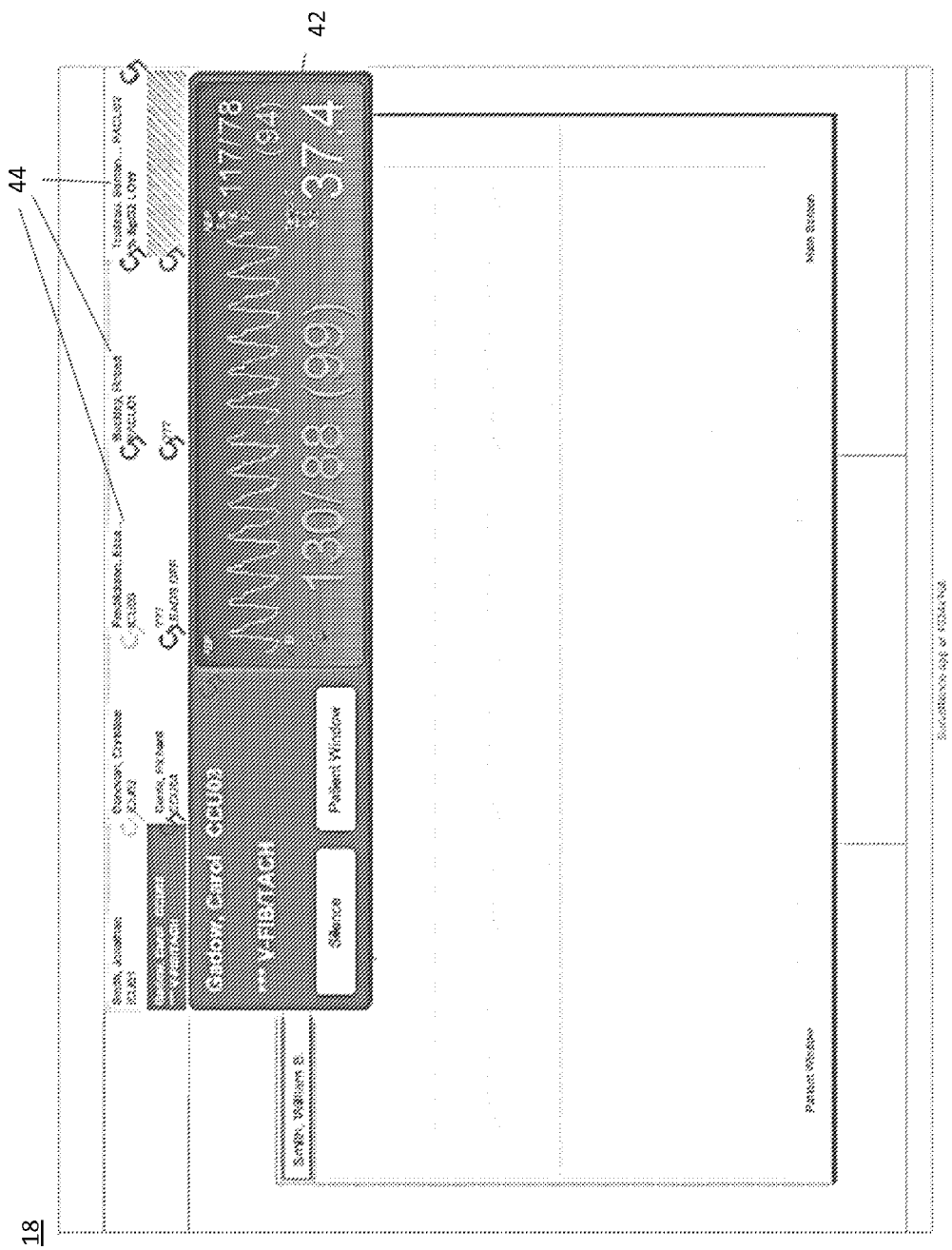
FIG. 4 is a ten sector display with sectors sent to the background with an auto-expand on alarm.
Figure 5:
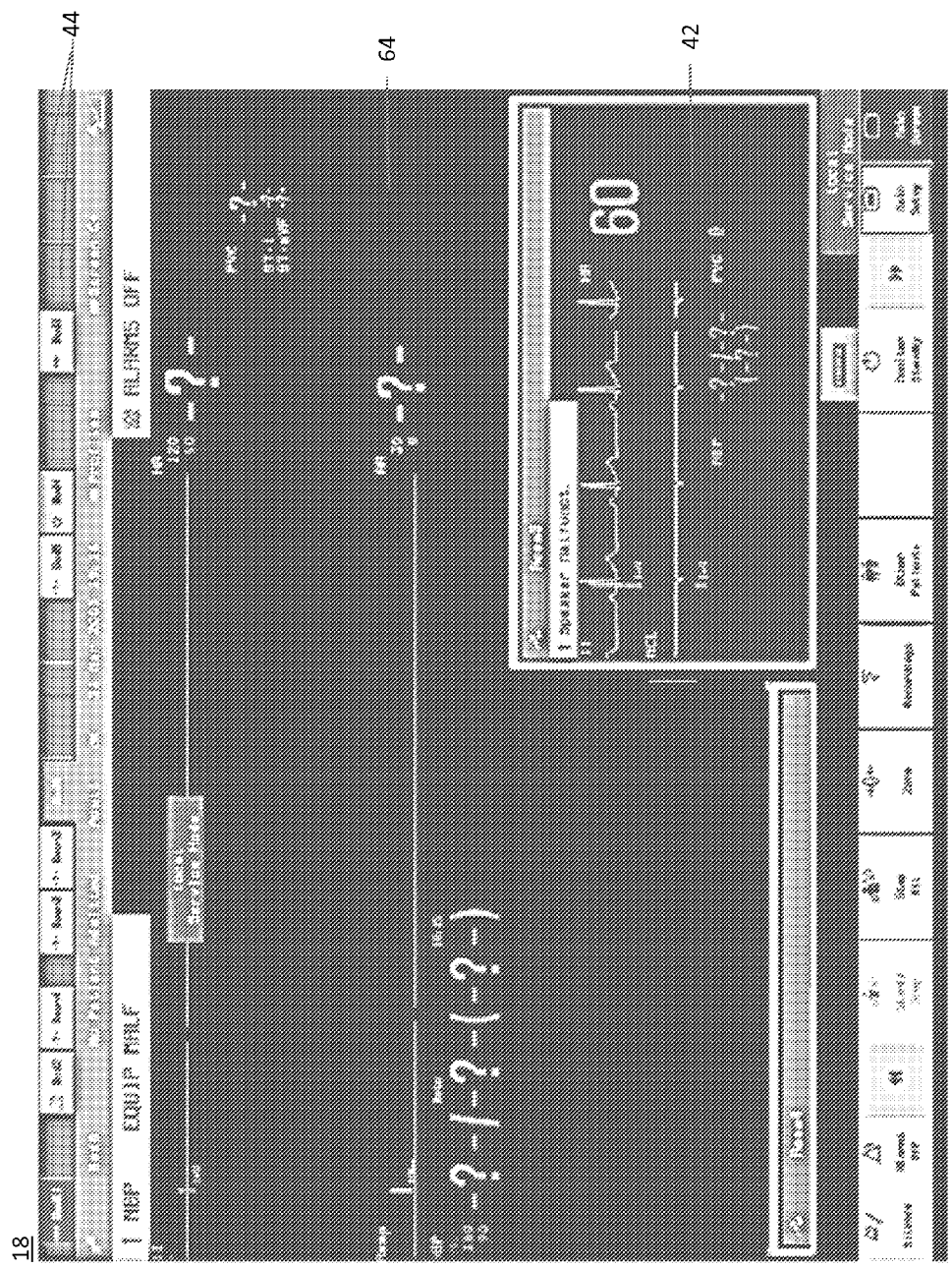
FIG. 5 is a patient display monitor within a bedside patient monitor.

FIGS. 4 and 5 illustrate a sector in the expanded format 42 alerting medical personal that a patient event or alarm condition has occurred regarding a specific patient. The sector corresponding to the patient sending physiological data indicative of a patient event or alarm is expanded in order to draw attention to medical personal that such a condition exists. The expanded format sector 42 is enlarged so that is it larger than the collapsed format 44 sectors, yet positioned so that it does not fully obscure any of the fully or partially collapsed format 44 sectors. The collapsed format 44 sectors need not necessarily be in a static area fixed to a certain location, but can be movable along the screen. The expanded format 42 sectors indicating a patient event or an alarm condition can temporarily overlap another expanded format sector 42 collapsed format sector 42 of a different patient. In another embodiment, the expanded format 42 sectors are resized such that all of the expanded sectors 42 are scaled to fit within a boundary of the display. In another embodiment, the patient monitoring station 10 monitors a very large plurality of patients. For example, an EGG patch which wirelessly connects with a hospital network can be attached to every patient. Although the patch is applied to a large number of patients, all the patients are monitored by collapsing the sectors of all of the patients. Any patient whose patch signal is indicative of a patient event or alarm automatically expands to alert medical personal of such a condition and/or other sectors collapse. A list canbe provided to the user to navigate to the patient, bed, or device and force the object of a sector or area.

FIG. 4 illustrates the patient monitoring station 10 in which the sectors 26 are configured in an auto-collapse mode and a collapse-to background mode. The sectors 26 receiving physiological data are in a collapsed format 42 and are attached to the background of the display 18. In FIG. 4, the bottom left sector has received physiological data indicative of an alarm condition and has been placed in an expanded format 42. The expanded format sector 42 is enlarged so that it is larger than the collapsed format 44 sectors, yet positioned so that it does not fully obscure any other sector 26. A plurality of sectors can be expanded concurrently to a uniform or non-uniform size, color, or transparency that is related to the severity of the patient's condition. The expanded form of the sector 42 can be displayed as a transparent object so the user can visualize the presence of another alert or event below the area consumed by the expanded area. Optionally, this window is movable or draggable by the user. FIG. 5 illustrates the patient monitoring station 10 in a bedside patient monitor. The physiological data being monitored by bedside monitor is displayed in the background 64 of the display 18. Remote medical devices 8 and patient beds 12 of the same hospital wing or floor are displayed in sectors with the collapsed format 44 so that a doctor may monitor all the patients of the wing or floor while at a patient's bedside. In response to a patient event or alarm condition of one of the other patients in the same hospital or floor, the sector corresponding to the patient with the event or alarm condition expands to the expanded format 42. In another embodiment, the display 18 of the patient monitoring system 10 is the display of a PDA, PC, tablet PC, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A patient monitoring station for monitoring a plurality of patient beds comprising:
   a display that concurrently displays a plurality of sectors;
   a controller configured to automatically create the sectors, each sector having an initial size sector format and each sector corresponding to one or more medical devices configured to be connected to a patient assigned to a patient bed, and to generate display data indicative of patient data in a corresponding sector of the display when patient data is received from the one or more remote medical devices, the controller programmed to:
   determine whether the received patient data is indicative of a patient healthcare event, a change in healthcare state, or an alarm related to the patient's medical condition;
   automatically resize the corresponding sector to a larger size sector format in response to the patient data being indicative of the patient healthcare event, the change in healthcare state, or the alarm related to the patient's medical condition;
   at least one of automatically displaying the larger size sector in the larger size sector format at least partially transparent; and
   automatically resize the size of the larger size sector to its initial size sector format in response to one of (1) the controller no longer receiving patient data or (2) the patient data no longer being indicative of the pending patient healthcare event, the change in health care state, or the alarm related to the patient's medical condition.

2. The patient monitoring station according to claim 1, wherein the controller is further programmed to:
   resize the sectors in the initial size sector format such that all the sectors in the initial size sector format are of a uniform size and resize the sectors in the larger size sector format such that all the sectors in the larger size sector format are of a uniform size, wherein the sectors are scaled to fit within a boundary of the display.

3. The patient monitoring station according to claim 1, wherein the controller is further programmed to: resize a size of the sector in the larger size sector format based on a severity of the alarm condition or time elapsed since the alarm condition, wherein the alarm condition is based on a measured physiological parameter in the patient data exceeding a time, severity, or escalation parameter.

4. The patient monitoring station according to claim 1, wherein the controller is further programmed to:
   control the display to represent a sector in the initial size sector format by a small object including a limited representation of the patient data; and
   control the display to represent a sector in the larger size sector format by a full representation of the patient data.

5. The patient monitoring station according to claim 1, wherein each sector in the initial size sector format is represented by a small object including a bed label, patient ID, or other representations of patient grouping, and a patient's highest priority monitored physiologic parameter, and wherein each sector in the larger size sector format is represented by a full size object including a full representation of the received patient data.

6. The patient monitoring station according to claim 1, wherein the display is incorporated in one or more of a PDA, tablet PC, and patient bedside monitor.

7. A patient monitoring system, the system comprising: one or more configured remote medical devices for measuring patient physiological parameters and generating patient data based thereon; and the patient monitoring station according to claim 1.

8. A method of displaying medical parameters, the method comprising:
   automatically creating a plurality of sectors, each sector having an initial size sector format;
   displaying medical parameters indicative of patient data received from one or more remote medical devices configured to be connected to a patient assigned to a patient bed in a corresponding sector of a display when patient data is received from the one or more medical devices;
   determining whether the received patient data is indicative of a patient healthcare event, a change in healthcare state, or an alarm related to the patient's medical condition;
   automatically resizing the corresponding sector of the display to a larger size sector format in response to the medical parameters being indicative of the patient healthcare event, the change in healthcare state, or the alarm related to the patient's condition;
   at least one of:
   automatically displaying the expanded larger size sector in the larger size sector format at least partially transparent; and
   automatically resizing the size of the larger size sector to its initial size sector format in response to one of (a) no longer receiving patient data and (b) the patient data no longer being indicative of the patient healthcare event, the change in healthcare state, or the alarm related to the patient's medical condition.

9. The method according to claim 8, further including:
   resizing the initial size sectors such that all the initial size sectors are of a uniform size and resizing the larger size sectors such that all the larger size sectors are of a uniform size, wherein the sectors are scaled to fit within a boundary of the display.

10. The method according to claim 8, further including:
    representing each initial size sector by a small object including a limited representation of the patient data; and representing an larger size sector by a full presentation of the patient data.

11. The patient monitoring station according to claim 8, further including:
    representing each initial size sector by a small object including a bed label, patient ID, and a patient's highest priority monitored physiologic parameter.

12. The method according to claim 8, further including:
    resizing a larger size sector based on a severity of the alarm condition or a time elapsed since the alarm condition, wherein the alarm condition is based on a measured physiological parameter in the patient data exceeding a time, severity, or escalation parameter.

13. The method according to claim 8, further including:
    automatically creating the plurality of sectors of the display, each sector corresponding to one patient.

14. The method according to claim 8, further including:
    programming any sector of the display to automatically resize the size of the larger size sector to its initial sizes sector format, automatically resize the size of an initial size sector to a larger size sector format, or collapse sector to the background of the display.

15. The method according to claim 8, wherein the display is incorporated in one or more of a PDA, tablet PC, and patient bedside monitor.

16. The method according to claim 8, further including:
determining whether each of the plurality of remote medical devices is sending patient data; and
determining whether the patient data indicates a patient healthcare event in response to a remote medical device sending patient data.

17. A non-transitory computer readable medium containing software which when loaded into a processor programs the processor to perform the method according to claim 8.

18. A patient monitoring system comprising:
a plurality of remote medical devices;
a patient monitoring system having a display and a controller programmed to perform the method according to claim 8.

19. A method of displaying medical parameters for a plurality of patients, the method comprising:
automatically creating one or more display sectors, each sector corresponding to a patient assigned to one or more remote medical devices configured to be connected to a patient assigned to a patient bed;
displaying medical parameters indicative of patient data received from one or more remote medical devices in a corresponding sector of a display when patient data is received from the one or more remote medical devices;
determining whether the received patient data is indicative of a patient healthcare event, a change in healthcare state, or an alarm related to the patient's medical condition;
automatically resizing the corresponding sector of the display to a larger size sector in response to the medical parameters being indicative of the patient healthcare event, the change in healthcare state, or the alarm related to the patient's medical condition; and
at least one of:
automatically displaying the larger size sector in larger size sector format at least partially transparent; and
automatically resizing the size of the larger size sector to its initial size sector format in response to one of (a) no longer receiving patient data and (b) the patient data no longer being indicative of the patient healthcare event, the change in healthcare state, or the alarm related to the patient's medical condition;
representing each sector in the initial size format by a small object including a limited representation of the patient data; and
representing a sector in the larger size format by a full presentation of the patient data.

* * * * *